(12) United States Patent
Ibrahim

(10) Patent No.: US 12,150,697 B2
(45) Date of Patent: Nov. 26, 2024

(54) CRYOPAD

(71) Applicant: AtriCure, Inc., Mason, OH (US)

(72) Inventor: Tamer Ibrahim, Danville, CA (US)

(73) Assignee: AtriCure, Inc., Mason, OH (US)

( * ) Notice: Subject to any disclaimer, the term of this patent is extended or adjusted under 35 U.S.C. 154(b) by 548 days.

(21) Appl. No.: 16/205,036

(22) Filed: Nov. 29, 2018

(65) Prior Publication Data

US 2019/0159835 A1 May 30, 2019

Related U.S. Application Data

(60) Provisional application No. 62/592,194, filed on Nov. 29, 2017.

(51) Int. Cl.
*A61B 18/00* (2006.01)
*A61B 5/283* (2021.01)
*A61B 18/02* (2006.01)
*A61B 18/12* (2006.01)
*A61B 18/14* (2006.01)
(Continued)

(52) U.S. Cl.
CPC .......... *A61B 18/1492* (2013.01); *A61B 5/283* (2021.01); *A61B 18/02* (2013.01); *A61B 18/1206* (2013.01); *A61B 2018/00011* (2013.01); *A61B 2018/00041* (2013.01); *A61B 2018/00101* (2013.01); *A61B 2018/0016* (2013.01); *A61B 2018/00214* (2013.01); *A61B 2018/00267* (2013.01); *A61B 2018/00291* (2013.01); *A61B 2018/00351* (2013.01); *A61B 2018/00363* (2013.01); *A61B 2018/00577* (2013.01); *A61B 2018/00589* (2013.01); *A61B 2018/00595* (2013.01); *A61B 2018/00791* (2013.01); *A61B 2018/00839* (2013.01); *A61B 2018/0212* (2013.01); *A61B 18/082* (2013.01);
(Continued)

(58) Field of Classification Search
CPC .. A61B 2018/00214; A61B 2018/0022; A61B 2018/00226; A61B 2018/00232; A61B 2018/0025; A61B 2018/00255; A61B 2018/00244; A61B 2018/00166; A61B 2018/0262; A61B 2018/0268; A61B 2018/0281; A61B 2018/00023
See application file for complete search history.

(56) References Cited

U.S. PATENT DOCUMENTS 5,151,100 A * 9/1992 Abele .................... A61B 18/08
607/113
6,251,065 B1 * 6/2001 Kochamba ............. A61B 17/02
128/898
(Continued)

OTHER PUBLICATIONS

Annotated Sperling900 Fig 4B (Year: 2022).*

*Primary Examiner* — Thomas A Giuliani
*Assistant Examiner* — Nicholas S Borsch
(74) *Attorney, Agent, or Firm* — Levine Bagade Han LLP

(57) ABSTRACT

Devices, systems, and methods for therapeutically treating tissue. The devices and methods are suitable for minimally invasive surgery or open surgical procedures. More particularly, methods and devices described herein permit treating large areas of tissue with a therapeutic device. In some variations, the method and devices allow for large area treatment without having to reposition the device. The methods and devices described herein discuss the treatment of cardiac tissue for purposes of illustration.

11 Claims, 13 Drawing Sheets

(51) Int. Cl.
  *A61B 18/08* (2006.01)
  *A61B 18/18* (2006.01)
  *A61B 18/20* (2006.01)
  *A61B 18/24* (2006.01)

(52) U.S. Cl.
  CPC .......... *A61B 18/1815* (2013.01); *A61B 18/20* (2013.01); *A61B 18/24* (2013.01)

(56) References Cited

U.S. PATENT DOCUMENTS

| | | | |
|---|---|---|---|
| 8,347,891 B2* | 1/2013 | Demarais | A61B 18/18 607/101 |
| 8,805,466 B2* | 8/2014 | Salahieh | A61B 18/1492 606/41 |
| 9,308,042 B2 | 4/2016 | Whayne et al. | |
| 9,439,714 B2 | 9/2016 | Whayne et al. | |
| 9,808,280 B2 | 11/2017 | Whayne et al. | |
| 10,166,058 B2* | 1/2019 | Sperling | A61B 90/04 |
| 2007/0156138 A1* | 7/2007 | Eisele | A61B 18/1492 606/49 |
| 2007/0249991 A1* | 10/2007 | Whayne | A61B 17/0218 604/28 |
| 2009/0163910 A1* | 6/2009 | Sliwa | A61B 18/18 606/41 |
| 2012/0179150 A1 | 7/2012 | Whayne et al. | |
| 2014/0378968 A1* | 12/2014 | Sutermeister | A61B 18/1492 606/41 |
| 2015/0250538 A1 | 9/2015 | Whayne et al. | |
| 2015/0265338 A1 | 9/2015 | Whayne et al. | |
| 2017/0042612 A1 | 2/2017 | Whayne | |
| 2017/0042614 A1* | 2/2017 | Salahieh | A61M 25/1011 |
| 2017/0215942 A1 | 8/2017 | Whayne et al. | |
| 2018/0206900 A1* | 7/2018 | Sperling | A61B 18/1492 |

* cited by examiner

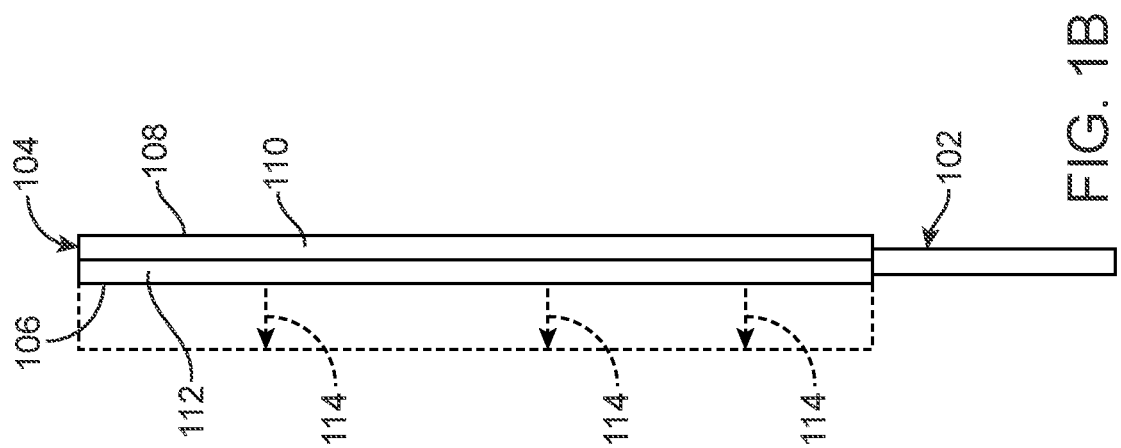
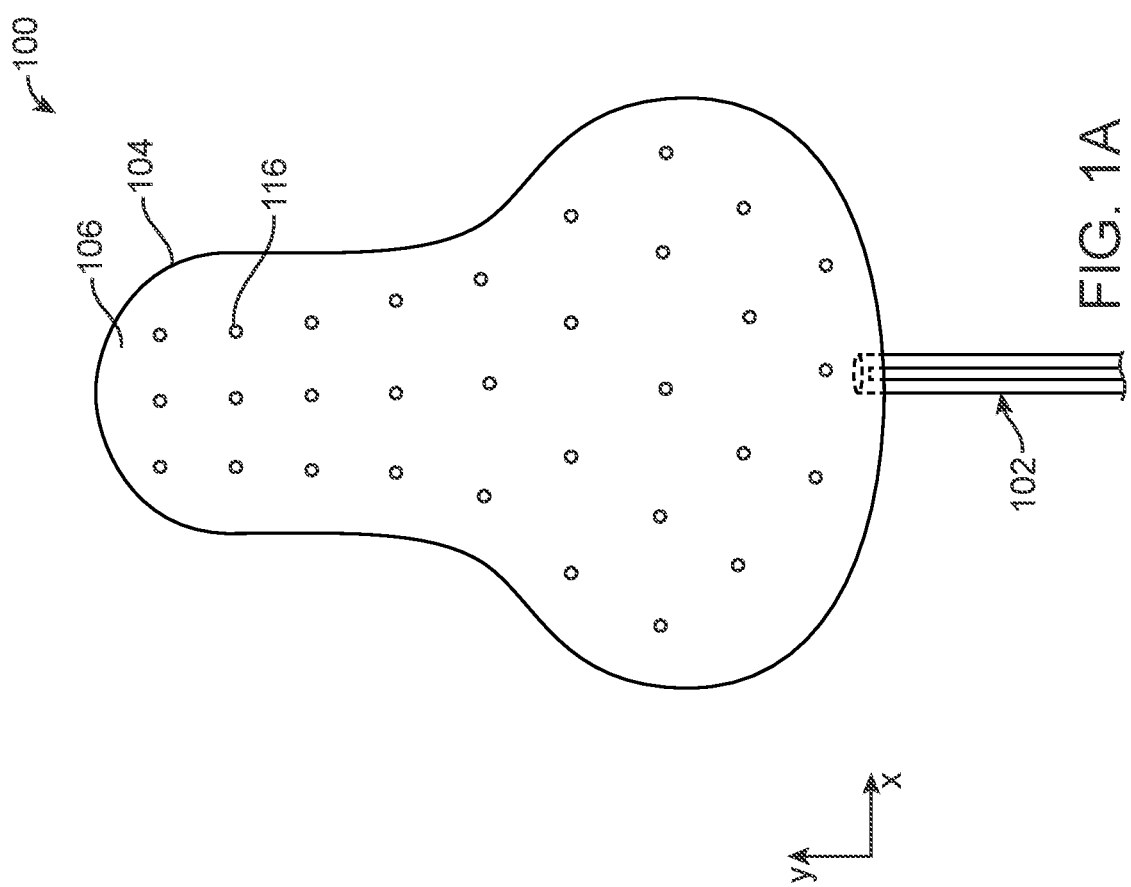

CRYOPAD

CROSS-REFERENCE TO RELATED APPLICATIONS

The present application is a non-provisional of U.S. Provisional Patent Application No. 62/592,194 filed on Nov. 29, 2017, the content of which is incorporated herein by reference in its entirety.

FIELD OF THE INVENTION

Methods and devices are disclosed herein for therapeutically treating tissue. The devices and methods are suitable for minimally invasive surgery or open surgical procedures. More particularly, methods and devices described herein permit treating large areas of tissue with a therapeutic device. In some variations, the method and devices allow for large area treatment without having to reposition the device. The methods and devices described herein discuss the treatment of cardiac tissue for purposes of illustration. However, the methods and devices can be applied in any application where tissue is treated (e.g., via such modes including heating, cooling, mechanical).

BACKGROUND OF THE INVENTION

Atrial fibrillation surgery requires creation of an ablation or coagulation lesion in atrial tissue. Typically, a physician creates a lesion using energy (including but not limited to cryogenic, radiofrequency, D.C., microwave, laser or other thermal modalities) to prevent wavelets or electrical signals/impulses that propagate through the atrial tissue to sustain atrial fibrillation or produce atrial flutter, atrial tachycardia, or another arrhythmia.

Many conventional approaches in applying energy to the atrial tissue face difficulties in attempting to create a complete lesion pattern that prevents propagation of the electrical impulse across the lesion pattern. Some factors attributable to these difficulties are tissue contact throughout the length of the electrode(s) is/are not consistent causing variability in the transmission of energy throughout the target length of ablated/coagulated tissue. Moreover, surrounding anatomic features also contributes to the difficulty in creating a complete lesion pattern. As a result, an incomplete lesion or lesion pattern includes one or more gaps of viable or semi-viable tissue that allows propagation of wavelets through tissue and through the lesion pattern.

Another factor in the inability of existing ablation systems to create complete curvilinear, transmural lesions is the presence of convective cooling on the opposite surface of the atrium. This convective cooling produces a heat sink that decreases the maximum temperature at this surface thereby preventing the lesions from consistently extending transmurally through the entire wall of the atrium. This is especially relevant during beating-heart procedures in which the coagulation/ablation probe is placed against the epicardial surface, and blood flowing along the endocardium removes heat thus producing a larger gradient between temperature immediately under the electrodes along the epicardium and that the temperature at the endocardium.

Yet another other deficiency of current approaches is the inability to direct the coagulation of precise regions of soft tissue while avoiding underlying or nearby tissue structures. For example, atrial fibrillation ablation may involve extending a lesion to the annulus near which the circumflex, right coronary artery, and coronary sinus reside; another example involves ablating ventricular tachycardia substrates that reside near coronary arteries or coronary veins. Conventional approaches are unable to selectively ablate desired soft tissue structures and isolate preserved tissue structures from targeted regions.

Traditionally, atrial coagulation patterns were only completed using endocardial coagulation lesions. In such procedures, the physician introduced one or more intravenous catheters through the vasculature to atrial tissue. Endocardial coagulation suffers a drawback in that the physician cannot easily visualize the site being ablated. Furthermore, endocardial coagulation carries a risk of complications due to ablating outward from the endocardial surface including esophageal fistula, thromboembolic complications from coagulum formation, PV stenosis, phrenic nerve palsy and lung damage. Aside from the risks, it is difficult to create complete linear lesion lines via an endocardial approach.

Recently, systems have been developed to ablate the cardiac tissue on the epicardium. Epicardial coagulation allows for more comprehensive bi-atrial lesion patterns at the expense of procedural complexity and time. However, many current procedures require significant manipulation of other tissue structures to create the desired lesion pattern. For example, many procedures require one or more ports or trocars placed in a chest wall and/or deflation of a lung to access the target site.

The ability to create lesions is further complicated in those situations where there is a desire to create a treatment pattern (e.g., ablation/coagulation) on a large area of tissue. In such cases, repositioning the device on the surface of tissue can lead to excessive overlap of treated tissue regions as well as increased procedure time. Furthermore, access to the region of tissue might be limited by the surrounding anatomy.

The improved methods and devices described herein offer an improvement to teach a large region of tissue, especially those organs those organs in the thoracic cavity. Variations of these methods and devices address the above described deficiencies for atrial fibrillation and ventricular tachycardia ablation. In addition, the embodiments or variations of the embodiments may address similar deficiencies, which are apparent during other applications involving coagulation of a selected tissue region in a precise manner.

U.S. Pat. Nos. 8,465,479, 8,241,273, 9,943,364, 888,766, 9,956,036, and patent application Ser. No. 15/954,070, the entirety of each of which is incorporated by reference, discusses the desirability of creating bi-atrial lesion patterns on opposing cardiac surfaces.

Such bi-atrial lesion patterns use both endocardial and epicardial lesions providing a technique that is comprehensive, bi-atrial and simpler than an epicardial or endocardial procedure alone.

U.S. patent application Ser. No. 15/224,346 discusses treating a large region of tissue, that increases coverage of the tissue surface area and can be reduced in diameter for entry or withdrawal at the site through an ordinary access cannula or catheter.

The improved methods and devices described herein offer improved access to tissue regions within the body, especially those organs in the thoracic cavity. Variations of these methods and devices described herein improve on the ability to treat atrial fibrillation and ventricular tachycardia ablation and can treat selected tissue regions in a precise manner.

SUMMARY OF THE INVENTION

The present disclosure includes methods and devices for treating a surface area of tissue. For example, such a device can include a catheter body having a working end; a flexible body located at the working end of the catheter, the flexible body having a expanse shape having a first expanse surface opposite to a second expanse surface, wherein the first expanse surface is configured to transmit energy to the surface area of tissue, where the flexible body is configured to assume a rolled configuration; a first chamber within the flexible body and adjacent to the first expanse surface; a second chamber within the flexible body and adjacent to the second expanse surface, wherein the second chamber is fluidly isolated from the first chamber; a plurality of sensing elements adjacent to the first expanse surface and configured to detect electrical activity in the surface area of tissue; and wherein delivery of a fluid through the catheter and into the second chamber causes the flexible body to move from the rolled configuration to the planar configuration and also causes expansion of the second chamber to move the second expanse surface in a direction away from the first expanse surface such that adjacent tissues are further spaced from the surface area of tissue.

An additional variation of the device can further comprise a source of cooling fluid fluidly coupled to the first chamber, such that delivery of the cooling fluid to the first chamber causes ablation to the surface area of tissue through the first expanse surface.

Variations of the device can further include at least one energy element on the first expanse surface, where the at least one energy transfer element causes ablation of the surface area of tissue. Such energy elements can comprise an RF electrode, a resistive electrode, a microwave antenna, an electroporation electrode, or a combination thereof. The plurality of sensing elements can be spaced in an array configuration adjacent to the first expanse surface.

An additional variation of the device can further include at least one suction port opened on the first expanse surface, where the at least one suction port permits application of a vacuum therethrough to secure the first expanse surface to the surface area of tissue. Variations of the device can further include a plurality of suction ports arranged on in a linear profile and is configured to engage the surface area of tissue when the flexible body is in the rolled configuration. Alternatively, or in combination, a plurality of suction lines can be exposed at a perimeter of the first expanse surface.

In additional variations of the device, the flexible body comprises a first section having a first width and a second section having a second width, where the first width is less than the second width for positioning between pulmonary veins on an atrial surface.

Some variations of the device can include a second expanse surface that comprises a thermally insulative surface.

Variations of the device can further include at least one spline member within the flexible body.

The present invention also includes methods of ablating surfaces of tissue. For example, one variation of such a method includes ablating an epicardial atrial surface of tissue in a patient. For example, such a method can include advancing a flexible planar ablation device in a rolled configuration to a location adjacent to the atrial surface, the planar ablation device having a first expanse surface opposite to a second expanse surface, wherein the first expanse surface is configured to transmit energy to the epicardial atrial surface; inflating a second chamber located in the planar ablation device and adjacent to the second expanse surface such that the flexible planar ablation device unrolls from the rolled configuration and the second chamber expands away from the epicardial atrial surface to separate adjacent tissues from the epicardial atrial surface; applying energy to the epicardial atrial surface using the first expanse surface to create an area of ablation in the epicardial atrial surface; and sensing electrical activity in the epicardial atrial surface using at least one sensing electrode on the first expanse surface assess the area of ablation for at least one gap in ablation.

A variation of the method can further include advancing a second ablation device within a heart of the patient to create additional regions of ablation to close the at least one gap.

Another variation of the method can include maintaining the flexible planar ablation device in a stationary position while advancing the second ablation device within the heart of the patient to create additional regions of ablation.

Variations of the access device and procedures described herein include combinations of features of the various embodiments or combination of the embodiments themselves wherever possible.

BRIEF DESCRIPTION OF DRAWINGS

FIG. 1A illustrates a variation of a device for treating a surface area of tissue.

FIG. 1B illustrates a side view of the flexible body and catheter.

DETAILED DESCRIPTION

Figure 2A:
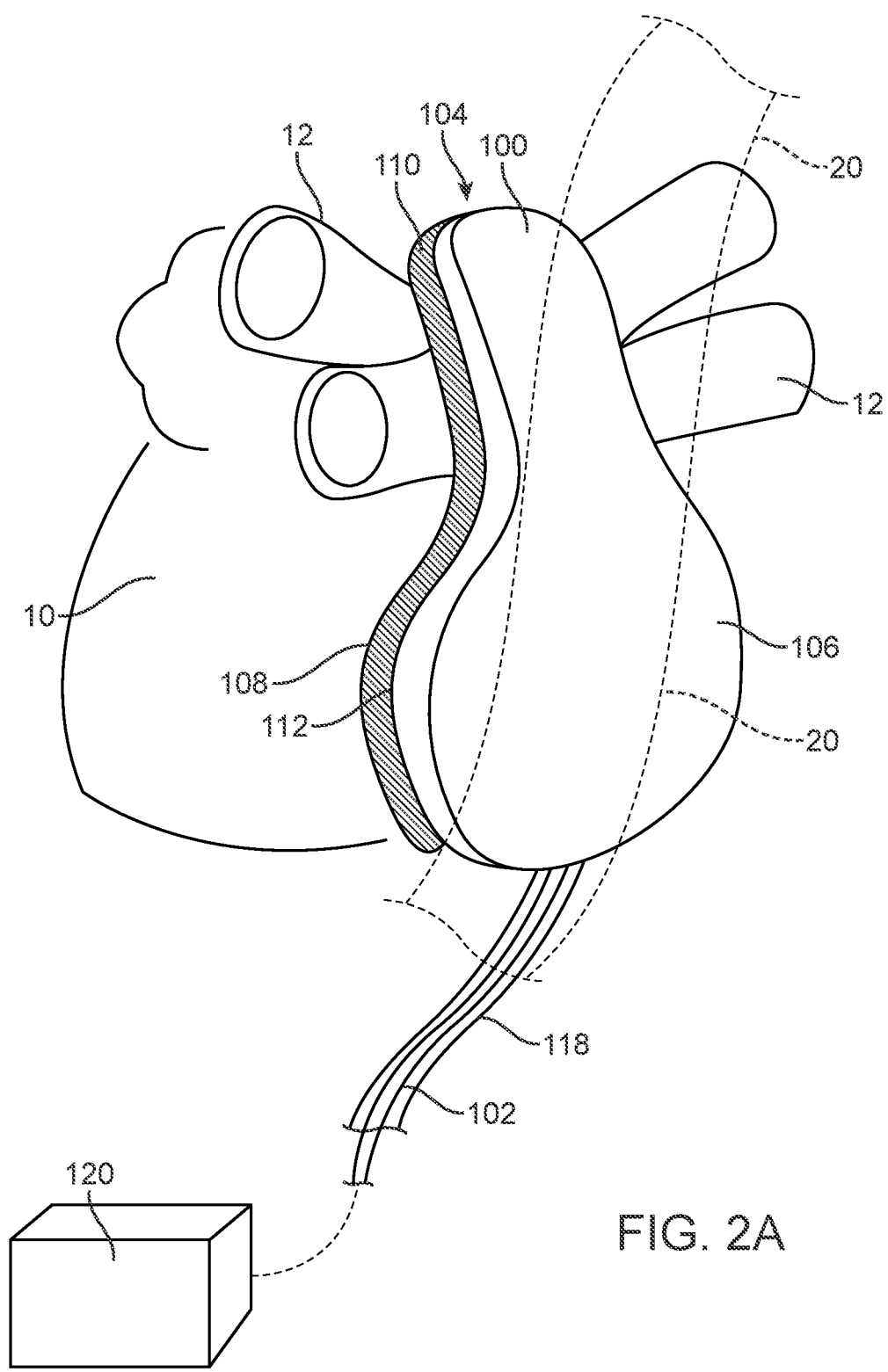
FIG. 2A illustrates a device that has been placed adjacent to a heart.

Methods and devices are disclosed herein for therapeutically treating tissue. The devices and methods are suitable for minimally invasive surgery or open surgical procedures. More particularly, methods and devices described herein permit treating large areas of tissue without having to reposition the treatment device. The methods and devices described herein discuss the treatment of cardiac tissue for purposes of illustration. However, the methods and devices can be applied in any application where tissue is treated (e.g., via such modes including heating, cooling, mechanical).

The devices described herein allow for creation of cardiac lesion patterns on cardiac surfaces. However, the methods and techniques are applicable to non-cardiac treatments as well. Variations of the devices, methods and procedures described herein include combinations of features of the various embodiments or combination of the embodiments themselves wherever possible.

Methods and devices described herein provide for treating regions of tissue with a device that increases coverage of the tissue surface area and can be reduced in diameter for entry or withdrawal at the site through an ordinary access cannula or catheter.

FIG. 1A illustrates a variation of a device 100 for treating a surface area of tissue. In certain variations, such as that shown in FIG. 1A, the variation of the device 100 is sized to treat a surface area of tissue that is greater than conventional ablation devices. In the illustrated variation, the device 100 is sized for positioning over an atrial surface.

As illustrated, the medical device 100 can include a catheter body 102 having a working end that is coupled to a flexible body 104. In general, the flexible body 104 comprises an expanse shape that is configured to treat tissue over an entirety or significant portion of the expanse shape. In most variations, the expanse shape comprises an uninterrupted or continuous area that is intended for positioning on the surface area of tissue to be treated. However, the expanse shape can include discontinuous regions 116 or interrupted regions so long as a significant portion, or all, of the shape can create a desired treatment effect in the tissue and/or separate and insulate tissue as described herein. Variations of the device can include an expanse shape that is planar, contoured, curved, and/or a combination of such profiles.

FIG. 1B illustrates a side view of the flexible body 104 and catheter 102. As shown, the flexible body 104 includes a first expanse surface 108 that is opposite to a second expanse surface 106. In the illustrated example, the first expanse 108 surface is configured to transmit energy to the surface area of tissue. As discussed below, the flexible body 104 is configured to assume a rolled configuration (it may be rolled in either the x-direction or y-direction).

As shown in FIG. 1B, the flexible body 104 includes a first chamber 110 within the flexible body and adjacent to the first expanse surface 108 as well as a second chamber 112 within the flexible body 104 and adjacent to the second expanse surface 106. In variations of the device, the second chamber 112 is fluidly isolated from the first chamber 110. However, variations of the device can include chambers that are fluidly coupled. FIG. 3B also illustrates a configuration where delivery of a fluid (either liquid, gas, or a combination thereof) through the catheter 102 and into the second chamber 112 causes the flexible body to move from the rolled configuration to a planar or spread configuration and also causes expansion of the second chamber 112 by moving the second expanse surface 106 in a direction 114 away from the first expanse surface 108 and first chamber 110. Expanding the second chamber 112 can further space adjacent tissues from the surface area of tissue to be treated. Alternatively or in combination, expansion of the second chamber 112 can provide further insulation to adjacent tissues to avoid unwanted collateral damage to tissue. Although not illustrated, catheter 102 can comprise a multi-lumen configuration to maintain fluid separation between chambers. Alternatively, two or more catheters can be used in alternate variations of the device.

The device 100 can also include one or more sensing elements 116 [106] adjacent to the first expanse surface and configured to detect electrical activity in the surface area of tissue. The sensing elements 116 can comprise any known electrode or sensor used for monitoring electrical activity within tissue.

Variations of the device 100 can include, an expandable member 104 that is mounted to a distal end of a steerable catheter. However, alternate variations include a catheter 102 that extends along a portion or entirety of the expandable member 104. For example, the catheter can extend within one or more chambers of the device, between chambers, or along the exterior of any of the expanse surfaces of the device.

FIG. 2A illustrates a device 100 that has been placed adjacent to a heart 10. In particular, the device 100 is positioned adjacent to an atrial surface of the heart 10 and between pulmonary veins 12. To achieve such positioning, the catheter 102 can be steerable or it can be introduced over a wire or through a sheath/access device 118. In use, the steerable catheter can be inserted percutaneously into the pericardium and directly to the oblique sinus of the heart 10. As shown, a distal end of the device 100 can reside at the posterior left atrium between the pulmonary veins 12. As shown below, the device 100 can be inserted adjacent to the atrium in a rolled or folded configuration and subsequently deployed such that the flexible body 104 unfolds or unrolls. The flexible body 104 can be sized to fill the space between the four pulmonary veins 12 and extending superiorly from any pericardial reflections, inferiorly to the coronary sinus. As discussed above, the second chamber 112 can be expanded with a fluid to unfold/unroll the flexible body 104, which also can cause expansion of the second chamber 112 away from the therapeutic expanse surface 108. This action also causes spacing of structures that are adjacent to the area intended for treatment, such as the esophagus 20. Next, a physician can apply energy at the therapeutic expanse surface 108 of the device 100. The fluid used to expand the first chamber as well as the therapeutic energy can be supplied by a controller 120 or multiple controllers. Furthermore, the controller (or a separate unit) can function as a venting system to evacuate/recirculate fluids from the chambers at the appropriate time.

As discussed above, the expandable body 104 can be constructed at least one chamber to fill space behind the heart or other organ intended for treatment. Further variations of the device can include more than two chambers. The expandable body 104 can be made of a variety of materials. Some variations of the device include one or both sides of the device to be made from a non-compliant material to constrain the size under high pressures. For example, the first chamber 110 is inflated with a thermally insulating media such as air. As noted above, the fluid media can also displace the left atrium from adjacent structures, such as the esophagus 20. The second chamber can be configured to contact and ablate the left atrium. In one embodiment, one or more injection tubes may be configured to introduce a cryogenic fluid, such as but not limited to liquid nitrogen, nitrous oxide, and/or argon into the ablation/second chamber of the expandable body. The second chamber may include at least one cooling circuit that may be designed to continually infuse cryogen into the expandable member. This may allow the cryogenic fluid to enter the chamber then back out into an exhaust system or outlet. This may be an open or closed loop system so that the cryogen may optimally and continually cool tissue. Once ablation is complete and the cryogen has been exhausted from the ablation chamber, a warm fluid can subsequently be introduced to defrost the expandable member. This warmer fluid may be available in the same cooling circuit or there may be a second cooling circuit to pump the warm fluid. Alternatively, defrost may occur by pressurizing the second chamber with a suitable fluid or simply by directing a second fluid through the chamber without causing a change in pressure.

Figure 2B:
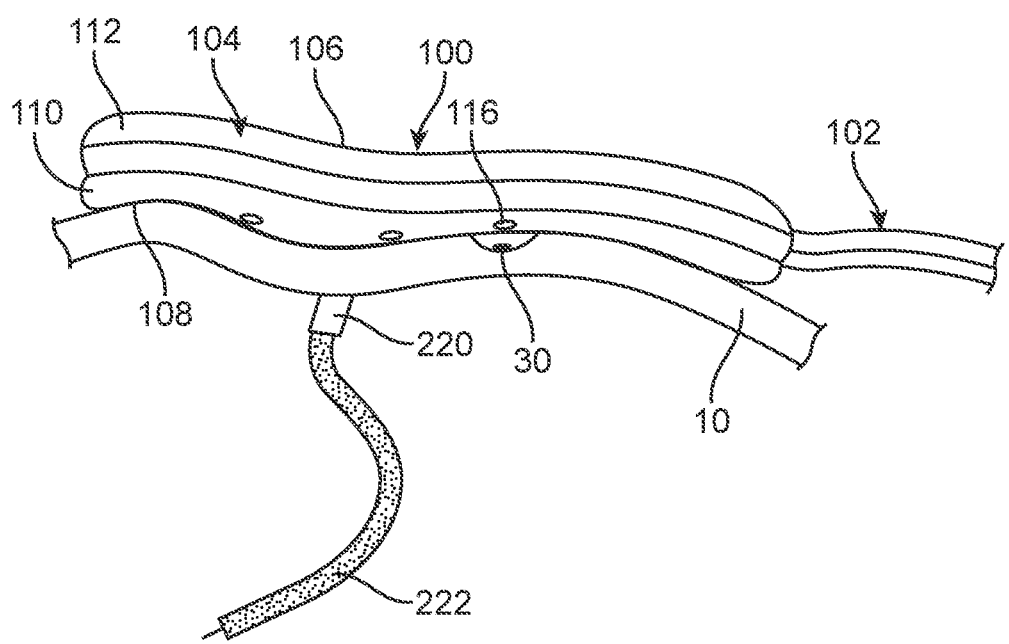
FIG. 2B illustrates a variation of a device positioned on an atrial surface and used to sense a gap in the tissue to provide additional treatment to prevent an electrical signal from propagating through the gap in cardiac tissue.

Additionally, the flexible body 104 may also be used to isolate the posterior wall during endocardial ablation to cover any ablation gaps. In procedures, electrophysiologists can isolate gaps in lesions through endocardial ablation (as discussed below). In such instances, heat might move through the posterior wall and into the esophagus. This increases the probability of esophageal injury. This injury can be prevented by using the flexible body 104 as a thermal protective layer as shown herein. In additional variations, the flexible body can be solid or fillable with a fluid, such as but not limited, to air or saline. FIG. 2B illustrates a variation of the device 100 positioned on an atrial surface 10 and used to sense a gap 30 where an electrical signal can propagate through cardiac tissue, which indicates that a gap in the tissue remains. The device 100, which is positioned on an epicardial surface of the heart 10, can be used with a second ablation device 222 advanced through an endocardial approach to create one or more lesions on the endocardial surface of tissue. Additionally, or in combination, the ablation device 222 can include a sensing means 220 to properly position the ablation device 222 opposite to the gap area 30 as identified by the device placed on the epicardial surface.

Figure 3:
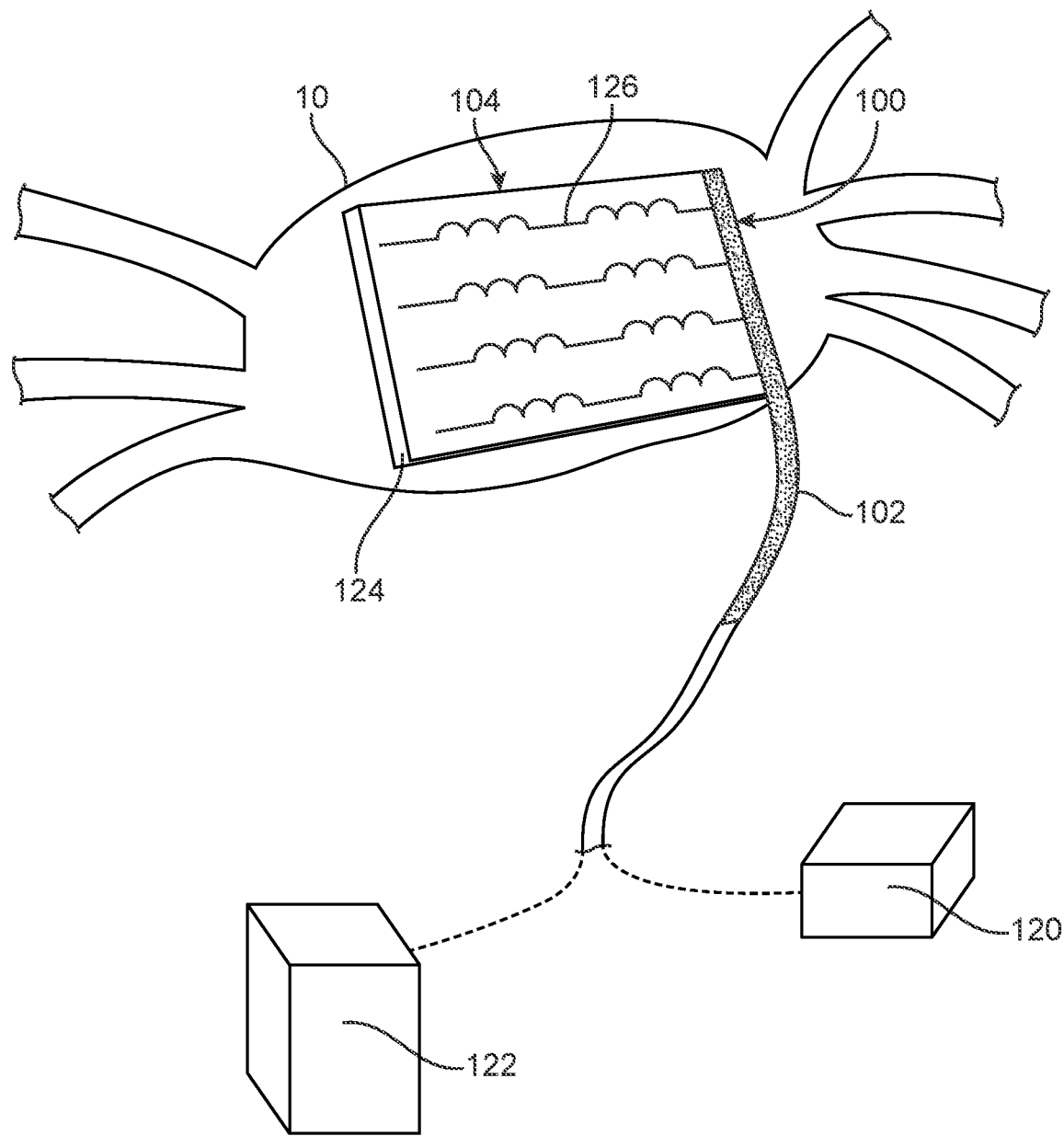
FIG. 3 shows a variation of a device that can include a series of electrodes or splines molded or affixed onto/into the flexible body such that energy can pass from the therapeutic side to the tissue.

Alternatively, or in addition, the second/therapeutic chamber can be configured to ablate using RF, microwave, resistive, electroporation or other modalities used for ablation or coagulation of tissue. For example, as shown in FIG. 3, a variation of a device 100 can include a series of electrodes or splines 126 molded or affixed onto/into the flexible body 104 such that energy can pass from the therapeutic side to the tissue. (For purposes of illustration, the first expanse surface is not shown). These electrodes 126 can facilitate functions of pacing, sensing, mapping and ablation when connected to the appropriate generators 122. FIG. 3 also illustrates an aspect of a device 100 in which the catheter 102 extends along a side of the flexible body 104. Such a feature can be useful for those variations of the device 100 including suction or vacuum lines 124 that are coupled to a vacuum source. In one example, the flexible body 104 can be rolled or folded such that the vacuum line 124 at the left-most side of the device can secure to tissue (in this example, the heart 10). Once properly positioned, the operator can unroll or unfold the flexible body 104 while leaving the end of the flexible body 104 attached to the tissue via the suction line 124.

Figure 4A:
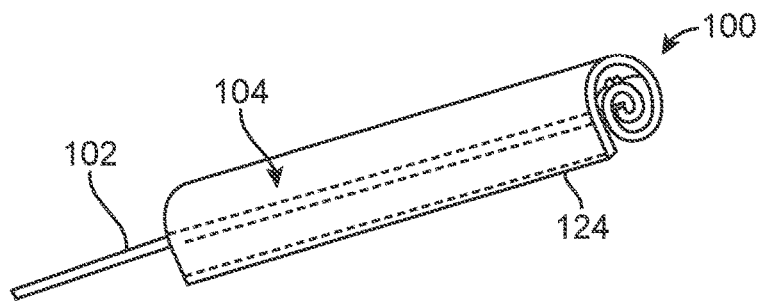
FIGS. 4A-4C illustrate another variation of a surface area treatment device.
Figure 4B:
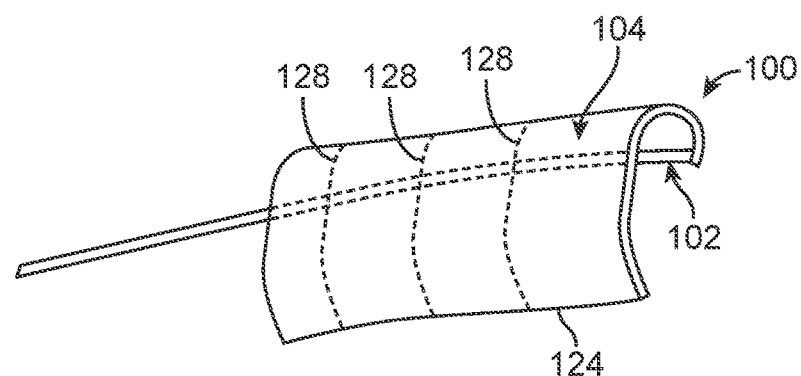
Figure 4C:
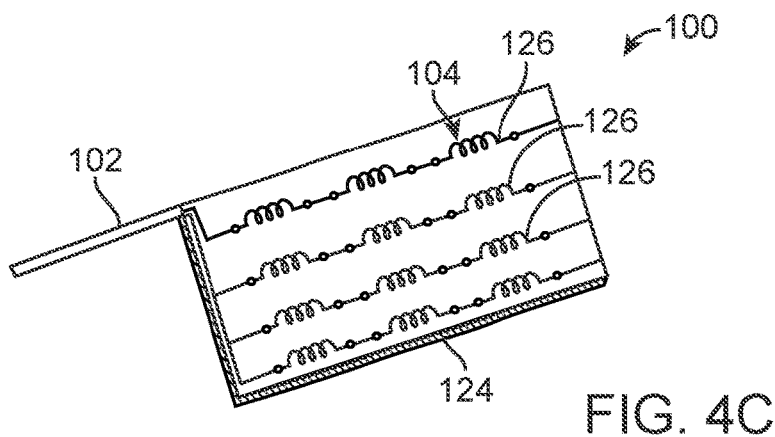

FIGS. 4A-4C illustrate another variation of a device 100. This variation of the device can include a flexible body 104 that has a single chamber, or is solid, but that can create a larger ablation pattern without moving to reduce surgical time. One benefit of such a device, as well as devices described herein, is to minimize the movement and repositioning of the therapeutic portion of the device during the procedure. As shown in FIG. 3A, the flexible body 104 can be rolled and unrolled (or folded and unfolded) for easy access, maneuvering, and positioning. The flexible sheet 104 can be constructed from a polymer sheet, such as but not limited to polyamide. To gain access to the target site, when used for a cardiac procedure, the rolled ablation body 104 can be introduced into the pericardial space by a sheath or another device known in the art.

Once in the epicardial space, the flexible body 104 can be placed along the back of the atrium using a suction line 124 within or attached to the body 104. In alternate variations, other mechanisms known in the art to provide suction may be implemented. As shown in FIGS. 4A and 4B, the illustrated device 100 shows only one suction line, however, more than one line may be used on the device 100. Alternatively, or in combination, the device can include multiple suction lines that are independently coupled to a vacuum source so that different portions of the body 104 can be affixed to tissue depending on positioning of the device.

FIG. 4B illustrates unrolling of the flexible body 104 while the suction line 124 holds one of the edges in position.

FIG. 4C illustrates a variety of elements 126 including ablation, sensing, and pacing. The device 100 can have the ability to power these elements at different times or simultaneously. In those variations of the device 100 not having an inflatable chamber, the material of the flexible body 104 can provide insulation to adjacent tissues. The ablation, sensing, and pacing elements may be constructed of materials known in the art.

In another variation, and as illustrated in FIG. 4B, a variation of the device 100 can include one or more shape memory alloys 128 extending along at least one or both lengths of the flexible body 104. The shape memory alloy frame 128 can be programmed to unroll when exposed to a specific parameter, such as body temperature (37° C.), via application of heat through the electrodes 126, and/or via delivery of a hot or cold fluid through the flexible body 104.

FIGS. 5A-5E illustrate another variation of an ablation device may have the ability to selectively inflate balloons or bladders affixed to an ablation device 200. The ablation device 200 can include any number of balloons or other expandable members 210 positioned about the device that allow for assisting in moving and positioning of the ablation device 200 on the posterior atrium. Inflating one balloon to the nearest anatomical border while deflating the opposing balloon may move the device and lock in place. Additionally, the balloons may assist in keeping the ablation device electrodes in correct plane (against epicardium) and thermally insulate surrounding structures. Additionally, the balloons may insulate non-target surrounding tissue.

Figure 5A:
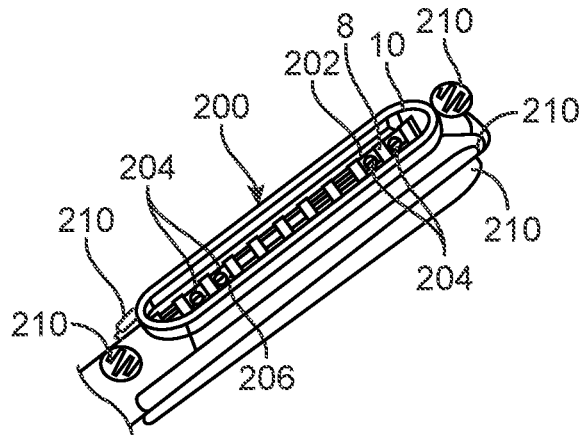
FIGS. 5A-5E illustrate another variation of an ablation device may have the ability to selectively inflate balloons or bladders affixed to an ablation device.

FIG. 5A illustrates a view of the distal end of an ablation device 200. In this variation, the device 200 includes a housing having both an energy transfer element 8 and a plurality of diagnostic element assemblies 202 and 206 exposed at the opening 10 of the housing. The illustrated variation shows device 200 having a coiled energy transfer element 8 with two diagnostic element assemblies 202 and 206. However, additional variations of probes can include a non-helical energy transfer element 8 with any number of diagnostic element assemblies or even a single assembly. As shown, electrodes 204 on the diagnostic element assemblies 202, 206 are positioned between the electrode or element surface (in this case the turns of the coil.) The housing 3 can also include any number of balloons 210 positioned about the device 200. Examples of coagulation devices that can be used with such balloons for creating lesions are disclosed in: U.S. Pat. No.: 6,893,442 filed on Jun. 14, 2002 issued on May 17, 2005; U.S. Pat. No. 7,063,698 filed on Apr. 29, 2003 issued on Jun. 20, 2006; U.S. Pat. No. 7,410,487 filed on Mar. 30, 2005 issued on Aug. 12, 2008; U.S. Pat. No. 7,572,257 filed on Aug. 18, 2005 issued on Aug. 11, 2009; U.S. Patent Publication No.: US 2006-0200124 A1 filed on May 23, 2006; US 2006-0206113 A1 filed on May 12, 2006; US 2006-0235381 A1 filed on May 12, 2006; US 2007-0043351 A1 filed on Apr. 21, 2006; US-2007-0250058-A1 filed on Apr. 19, 2007; US-2008-0114354-A1 filed on Nov. 9, 2006; US-2008-0114355-A1 filed on Nov. 9, 2006; US-2008-0243119-A1 filed on Jun. 6, 2008; and US-2009-0254009-A1 filed on Jun. 16, 2009. The entirety of each of which is incorporated by reference herein.

Figure 5B:
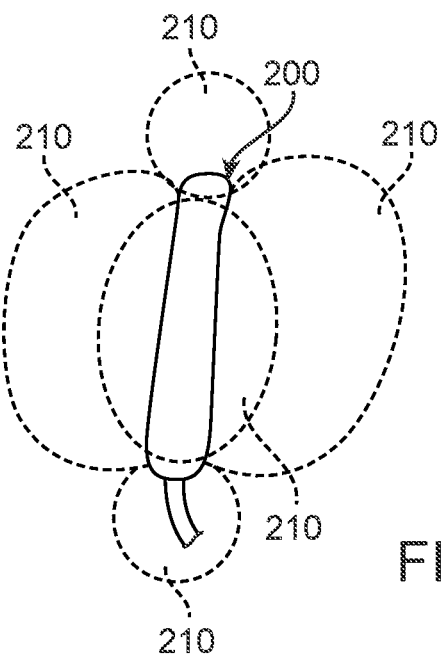

As show in the FIG. 5B, each of the balloons 210 can be inflated in any number of configurations or permutations to allow for positioning before or after creation of a treatment pattern. Additionally, other components such as vacuum may be added to the ablation device. Ablation energy may include but is not limited to visible light, coherent light, ultraviolet light, magnetic energy, and electrical energy. The ablation device may include but is not limited to RF energy device, a laser device, an infrared heating device, a chemical ablation device, a cryogenic device, a microwave energy device, and a resistive heating device.

Figure 5C:
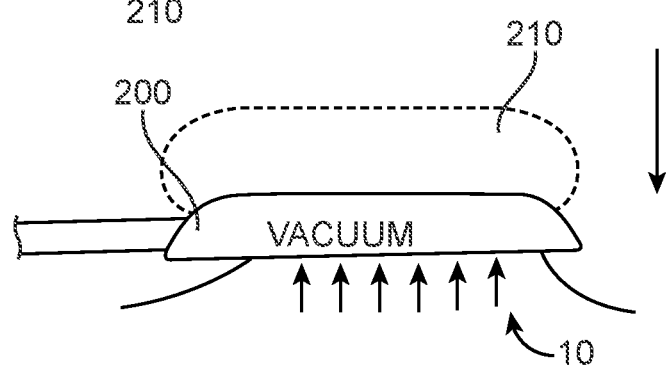

FIG. 5C illustrates a balloon 210 expanded on a surface of the device 200 that is adjacent to a tissue surface that is not intended for treatment. As shown, as the tissue 10 is drawn against the device 200, the balloon 210 can assist in keeping the device placed against the tissue or can serve to insulate and/or space adjacent tissue from the area being treated.

Figure 5D:
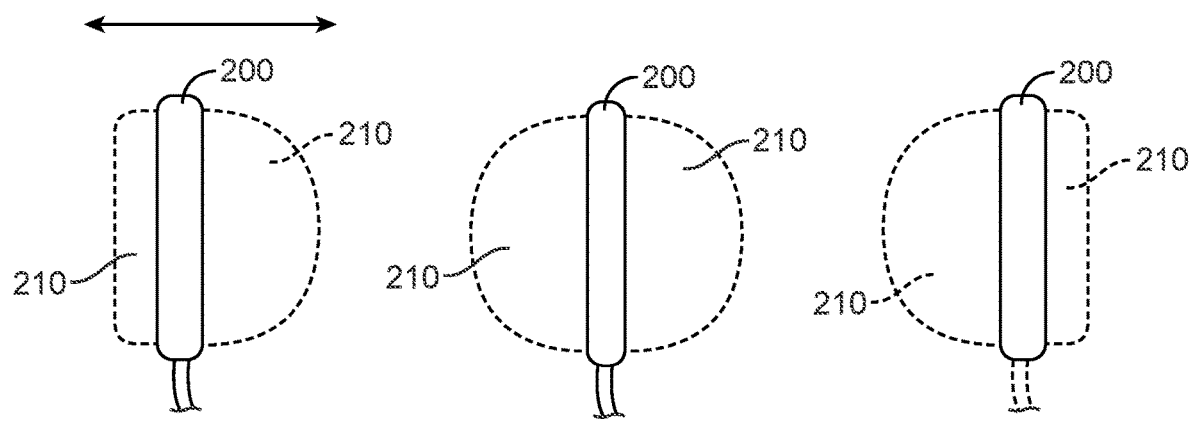
Figure 5E:
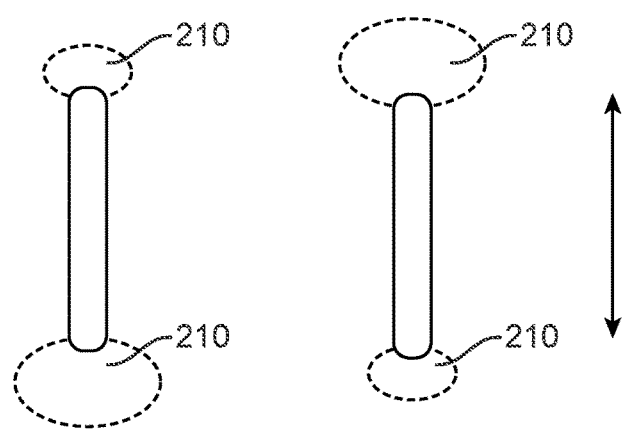

FIGS. 5D and 5E illustrate selective inflation of various balloons 210 to move the ablation device 200 in either a lateral direction, as shown in FIG. 5D, or an axial direction as show in FIG. 5E. The figures illustrate that the balloons can be selectively inflated as well as partially or fully inflated to assist in positioning. As such, the device 200 can be moved in lateral and/or axial directions by inflating the appropriate balloon to urge the device 200 and/or inflated balloon against tissue to cause movement of the balloon.

Ablation Atrium Catheter

Figure 6A:
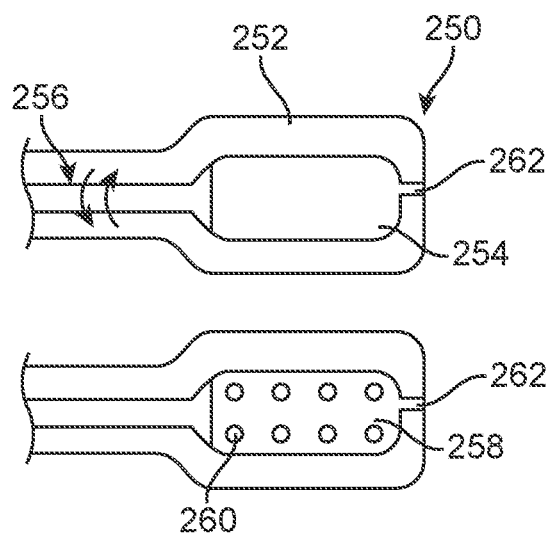
FIGS. 6A to 6D illustrates another variation of a treatment device that provides for a distal tip distal tip having a treatment surface and a sensing surface on an opposite side of the treatment surface.

FIGS. 6A to 6D illustrates another variation of a treatment device 250 This disclosure provides for a distal tip that may include distal tip irrigation, distal tip vacuum, distal tip RF ablation, distal tip cardiac sensing. As shown in FIG. 6A the device can include an insulative region or non-conductive outer layer 252 that, on a first side, is adjacent to a treatment region 254. The treatment region can include electrodes, or any structure as disclosed herein that applies therapeutic treatment to tissue. The shaft 256 of the device 250 allows for torqueing of the distal portion so that a sensing region 258, located on an opposite side to the treatment region 250, can be positioned adjacent to the tissue region of interest. The sensing region 258 can include any number of sensors or electrodes used to pace or stimulate tissue. The device can include one or more lumens 262 for advancement of a guidewire or delivery of fluid.

Figure 6B:
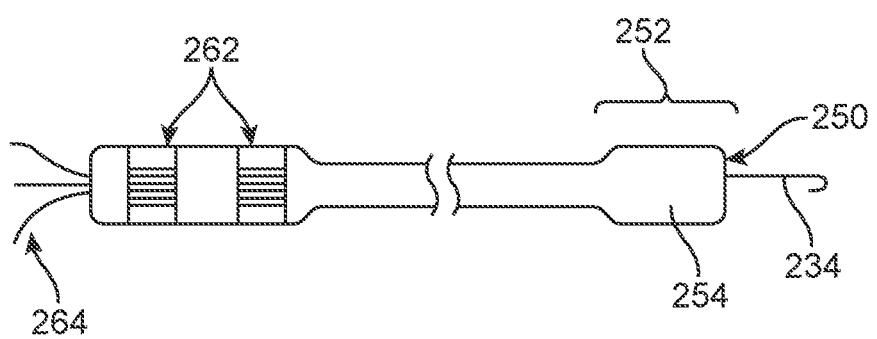
Figure 6C:
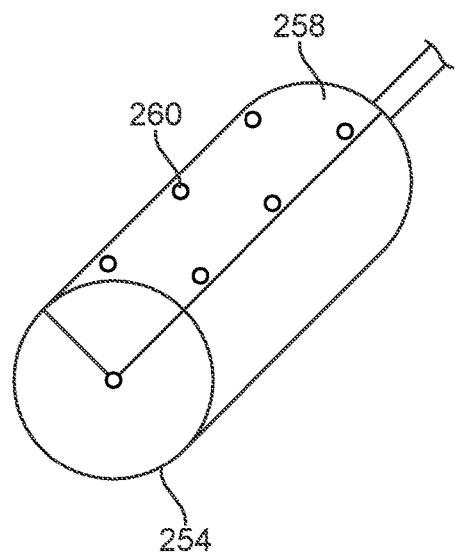

FIG. 6B illustrates the device of FIG. 6A with the insulative region 252 surrounding the treatment region 254 as the device 250 is advanced over a guidewire 234. The device can include a handle having any number of controls that allow for control of deflection and/or rotation of the distal portion of the device 250. Furthermore, the handle can include any number of fittings 264 to allow fluid coupling to a vacuum source, a fluid/liquid source as well as an energy source or controller.

This variation of the device can include a distal tip with an ablation element 254 surrounded by shielding 252 to prevent ablation of the esophagus and other non-target tissue. The device and/or distal tip may be flexible or deflectable. FIG. 6B illustrates an end view of the device showing that the ablation region 254 is larger than the sensing region 258 allowing for the device to minimize the number of ablation sequences when applied to tissue. The ablation electrode may be rotatable about an axis of the catheter as shown in FIG. 6D.

Figure 6D:
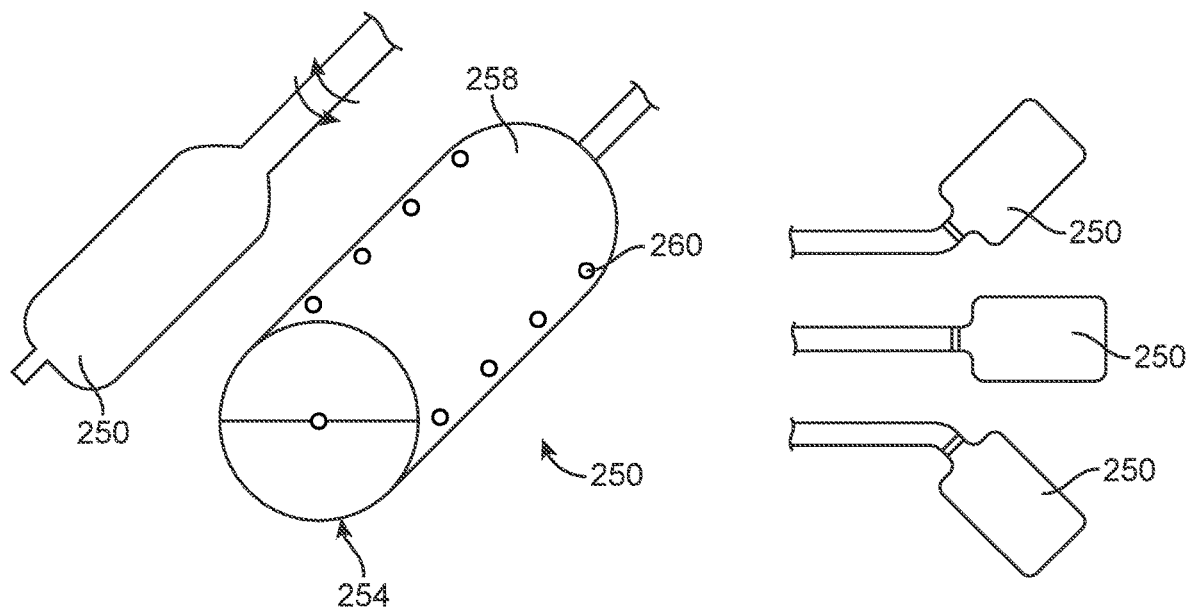

FIG. 6D also illustrates a variation of the device where ablation side 254 of device 250 is a continuous half-cylinder of conductive material, and the sensing side 258 of the device 250 has areas of conductive material 260 that are electrically isolated from each other. In one variation, the conductive areas 260 are circular; however, any shape may be used. The distal portion of the device 250 can be attached to an elongated flexible member that may connect to the distal tip and may attach to the proximal handle. The elongate flexible member can be composed of materials known in the art such as laser cut torque tubing. The elongated member may have the appropriate mechanical stop to prevent excessive rotation, and the handle may incorporate the appropriate interlocks, either mechanical or electrical, to prevent inappropriate ablation energy delivery to non-target tissue. Additionally, the distal tip electrode assembly may include cooling pathways, which may allow various cooling fluids to flow in either an open or closed loop system. These cooling fluids may include and are not limited to water and saline. The distal tip may also include a vacuum line. Additional features include an inflatable structure like a balloon to assist in electrode placement. The tip assembly may also include other mechanical structures, such as wire or polymer extensions, that may assist in electrode placement. The images below show the ablation electrode as an elongated cylinder; however, other shapes may be used. This includes but is not limited to oval or flattened shapes.

Figure 7:
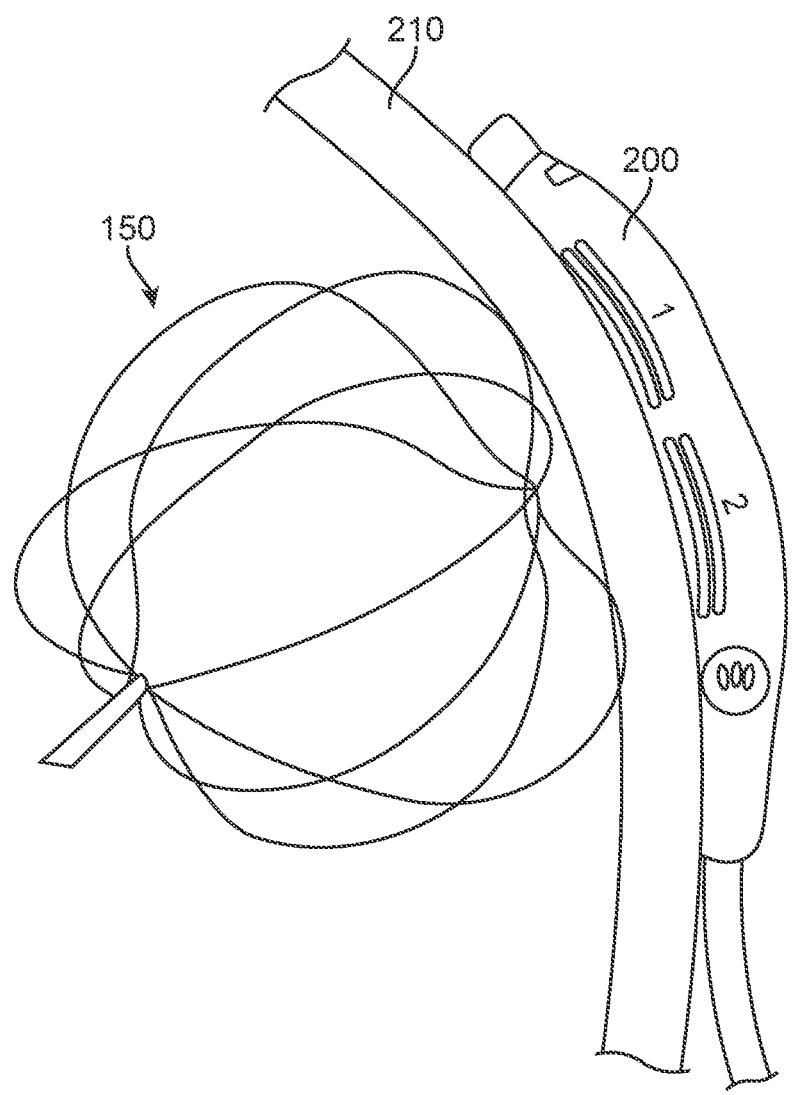
FIG. 7 illustrates the use of a basket catheter with a second ablation device to provide improved treatment of tissue.

FIG. 7 illustrates the use of a basket catheter 150 endocardially positioned adjacent to heart tissue 10 to provide 3D mapping and identify complex arrhythmias. The basket catheter 150 can be configured such that select splines are inactivated while other splines are activated. The active splines can be configured as a return path for an endovascular device 200 advanced within the heart 10, such as those described above, as well as radiofrequency system including, but not limited to, the COBRA Fusion and Epi-Sense devices. The expansion of the basket within the pericardial space may ensure contact of the electrode splines with the atrial tissue 10 while also providing esophageal shielding from the inactive splines by creating space and separate the atrial tissue being ablated from the esophagus or other adjacent structures.

Such an approach can enhance endocardial ablation of the posterior wall by EPs. In other embodiments, the basket catheter may be comprised of a balloon with electrode splines and could be used to provide esophageal protection and real time signal collection during endocardial ablation as a measure of transmurality.

In another variation, still referencing FIG. 7, a bi-polar bipolar system can use a basket catheter 150 as return electrode. Magnetically attracted endocardial and epicardial catheters have been previously described to enable EPs to create bipolar linear lesions. This variation uses an epicardial catheter 200, preferably applied with vacuum, and the basket catheter 150 configured as the return electrode catheter where by the nearest of a series of splines of the basket catheter would create the bipolar ablative effect.

Current practice requires EPs to create lesions endocardially in spot by spot applications with small movements. Lesion depth is limited because the catheter is monopolar with small tip electrode. EPs commonly avoid extensive ablation between the right and left PV sets due to concern of esophageal injury. This variation uses a system similar to a COBRA Fusion or Epi-Sense vacuum applied electrode device; however, the electrode may be configured only as the return electrode. The energy delivered by the endovascular catheter may be become bipolar. Vacuum may not be necessary for this device. The COBRA Fusion or Epi-Sense vacuum applied electrode device may be visible with common imaging modalities and may provide a landmark for the EP to perform linear lesions. COBRA Fusion or Epi-Sense vacuum applied electrode device would provide insulation from surrounding structures. This may be enhanced with irrigation or cooling internal to the COBRA Fusion or Epi-Sense vacuum applied electrode device or from an inflation structure integrated to the backside of the COBRA Fusion or Epi-Sense vacuum applied electrode device (as described above) to cause separation from surrounding structures. The inflation structure may be filled with any fluid known in the art to provide cooling.

Conforming Probe with Auto-Lift Feature

Figure 8A:
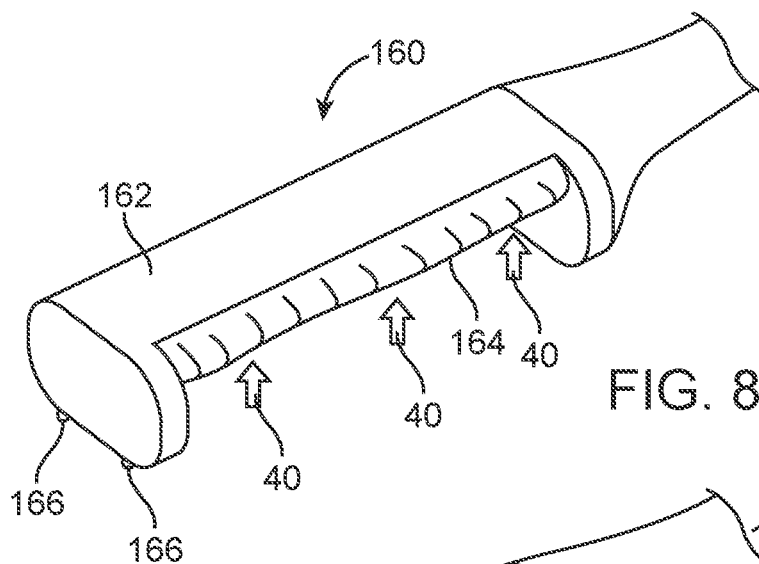
FIGS. 8A to 8E illustrates an additional variation of an ablation device 160 that conforms to tissue for treatment but provides an insulative region to protect adjacent tissues.
Figure 8B:
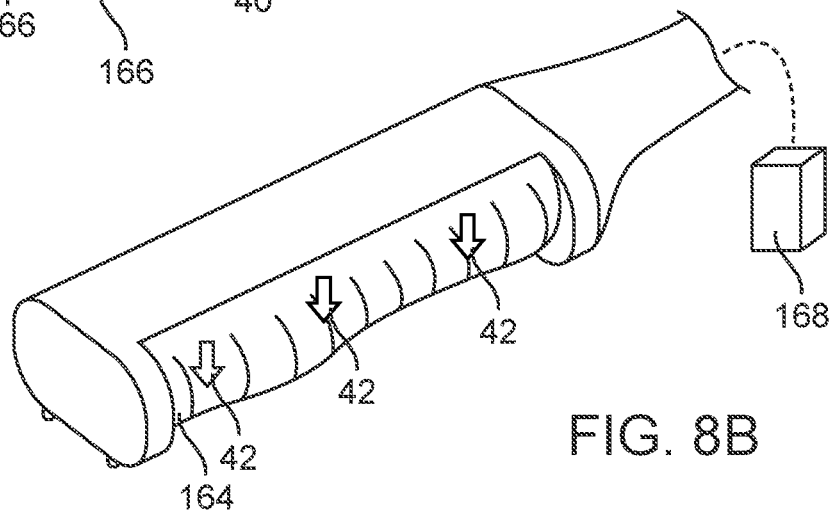
Figure 8C:
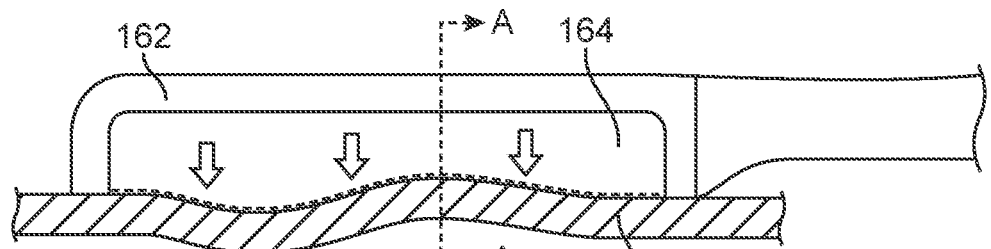
Figure 8D:
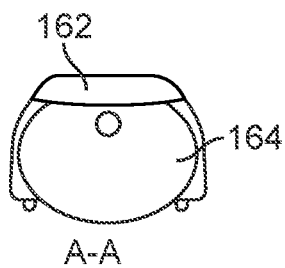
Figure 8E:
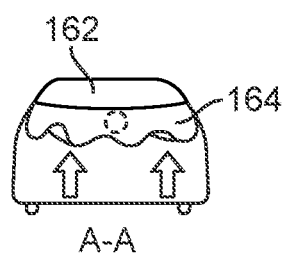

FIGS. 8A to 8E illustrates an additional variation of an ablation device 160 that conforms to tissue for treatment but provides an insulative region to protect adjacent tissues. As illustrated, the device 160 can include a bridge-like frame 162 that provides some degree of insulation. The frame 162 can be rigid or flexible and houses an inflatable structure, such as a balloon or bladder 164, within the frame 162. The inflatable structure 164 can be affixed to the top underside surface of the frame 162 such that as the inflatable structure 164 fills with a fluid via fluid source 168, as shown in FIGS. 8B and 8D, it moves in direction 42 to contact the tissue and can conform to any surface irregularities. When ablation cycle finishes, as shown in FIGS. 8A and 8E, the inflatable structure 164 deflates in direction 40 such that the inflatable structure 164 separates from tissue 10. The inflatable structure may be filled with any cryogen or fluid that allows it to contact tissue. The fluid can provide the energy, either cryogenic or thermal, to perform the ablation. Furthermore, in an alternate variation, the surface of the inflatable structure 164 can be conductive to facilitate energy transfer while the fluid facilitates conformation against contoured tissue as shown in FIG. 8C. The bridge or frame 162 can include any number of features 166 such as suction, pacing electrodes, or raised surfaces, to facilitate treatment and placement of the device.

In addition to cryoablation, the probe may provide radiofrequency, ultraviolet, microwave, or other ablative energy known in the art. The frame ends and the inflatable structure may have pacing and sensing electrodes. In other embodiments, the inflatable structure may provide cooling measure if using a non-cryogenic ablation energy such as radiofrequency.

Balloon Insulator

Figure 9A:
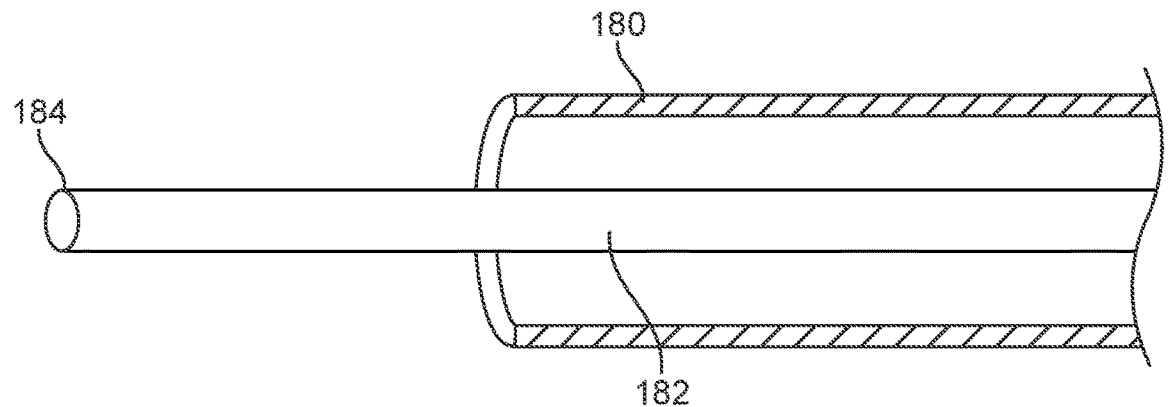
FIGS. 9A and 9B illustrate another system for ablation of tissue having a collapsible inflatable structure housed within a cryoprobe sheath.
Figure 9B:
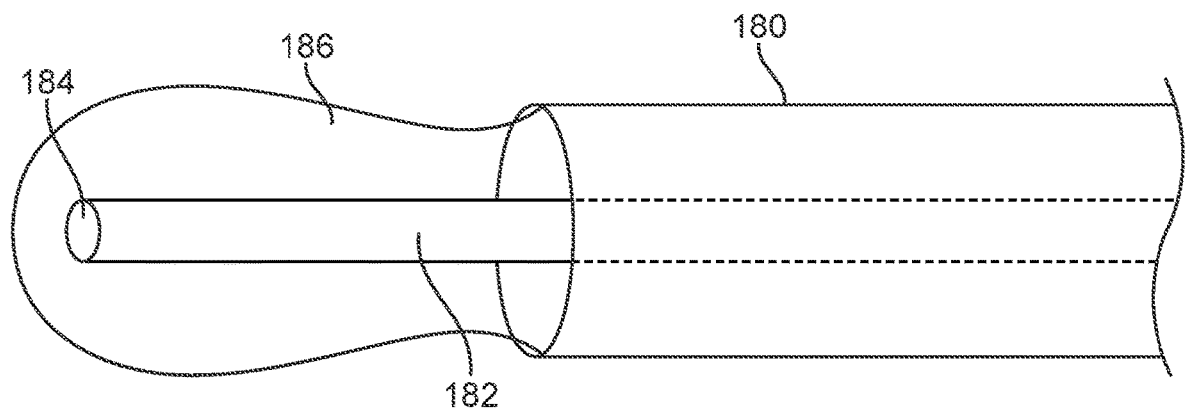

FIGS. 9A and 9B illustrate another system for ablation of tissue. In this variation, a collapsible inflatable structure (not shown in FIG. 9A) is housed within a cryoprobe sheath 180 or a separate tube of the cryoprobe may be mechanically advanced and expanded. As shown in FIG. 9B, the inflatable structure 186 can be advanced from the sheath 180 to form a pillow structure that allows the cryo probe 182 to be less impacted by the blood pool heat sink when ablating. The inflatable structure may be filled with a fluid, such as but not limited to air, saline, water. As shown in FIG. 9B, structure would become asymmetrical when the probe is pushed against tissue.

Over the Cryoprobe and Add-On Devices

Figure 10A:
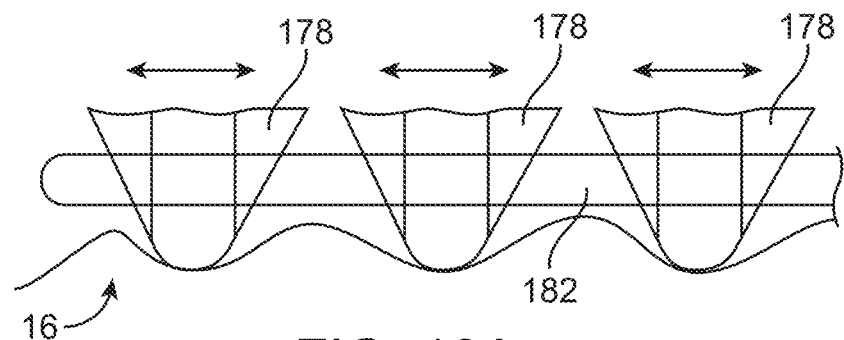
FIGS. 10A to 10C illustrate various add-on extensions for a cryoprobe to enhance and change the ablation capabilities.
Figure 10B:
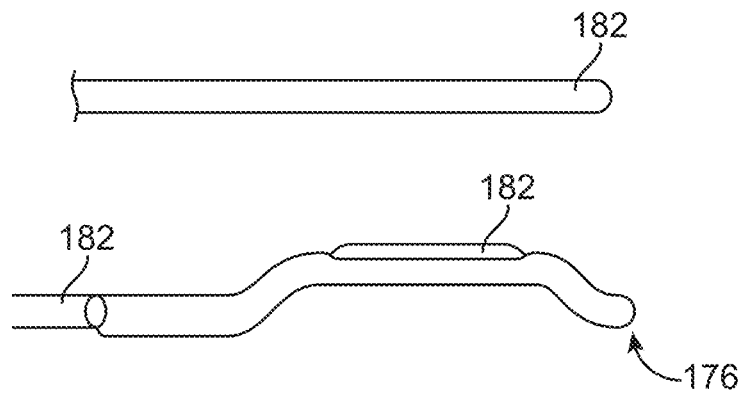
Figure 10C:
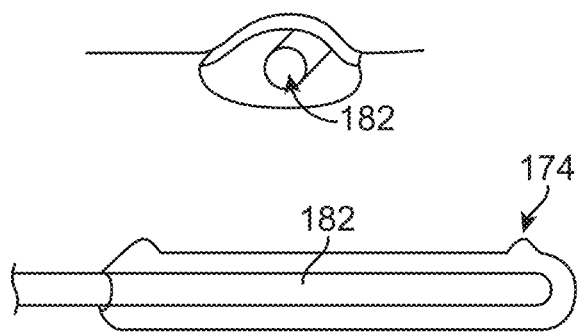

FIGS. 10A to 10C illustrate various add-on extensions for a cryoprobe 182 to enhance and change the ablation capabilities. For example, FIG. 10A shows multiple thermally conductive extensions 178 that allow a single probe 182 to create multiple simultaneous lesions over an active area of the probe that allows for heat transfer. The extensions 178 can optionally slide over the probe 182 and are thermally connected to the probe. The extensions may be positioned as needed such that at the point of contact with tissue 16 cryo energy conducted from the probe 182 through the extensions 178 ablates or treats tissue.

FIG. 10B illustrates another variation that focuses the energy from the cryoprobe 182 to a single line while insulating the back of the probe. In another example, the extensions may create a big foot for wide area ablation. As shown, the cryoprobe 182 is positioned within a shapeable insulator 176 (or the insulator can have a pre-determined shape). The cryoprobe 182 is exposed at a region in the insulator to control the area of treatment.

In another embodiment, the attached member may be expandable such as a mesh or even a thermally transferring balloon. Another embodiment may be a sharp point for percutaneous insertion. These concepts use power from the back of the probe which is normally wasted and bring to by thermal conductivity to the ablating surface. Any cryogen may be used with this cryoprobe and respective extensions.

FIG. 10C illustrates another enhancement to a cryo probe 182 that can have an insert 174 having groove shape with an insulated backing. The backing can be made from plastic with a heat transfer element insert (such as copper or aluminum) that transfers energy from the cryo device.

Epicardial Electro-anatomical Mapping/Ablation Systems and Methods

Sub-X access may be created using direct/endoscopic visualization. A suction wand may be attached to the pericardium to provide pericardial retraction such that the retracted pericardium can be safely incised with endoscopic instrumentation or cautery without risk perforating the heart. A dilating cannula may be placed and anchored to maintain access to the pericardial window for subsequent instrument introduction.

An epicardial roving catheter that may be used to perform voltage mapping and pace/activation mapping is described. The delivery system may be configured on the body of a steerable catheter or a rigid shaft with limited articulation capability. A suction cup with integrated electrodes/sensors would be configured to the distal end. The electrodes may contact the epicardium and as the catheter is moved around the surface topography, a 3D anatomical image is produced in conjunction with a SJM EnSite or comparable system.

Similarly, a magnetic sensor may be configured for use with the Carto system. Anatomical mapping can be performed in conjunction with direct endoscopic visualization which would be performed either by a separate "bird's eye" endoscope or with an integral rigid or flexible endoscope onto which the suction cup apparatus is mounted. In the latter case, the suction cup may also act as a spacer to prevent contact of tissue and bodily fluid with the lens.

For electrical mapping in which a reference catheter is useful, the reference catheter could be placed within the RV or LV at the apical location, or epicardially located at the apex via a second electrode mounted suction cup applicator. By moving the epicardial suction cup roving catheter while contacting the heart, a voltage map may be produced to identify scar locations. Further electrical pace mapping can then concentrate at the borders of the identified scar areas to more rapidly pinpoint target VT ablation sites.

Upon locating a target site, suction is activated to immobilize the ablation element with respect to tissue. Coronary angiography can be performed to confirm that the device is not adhered over a coronary artery if this confirmation cannot be achieved visually with endoscopes. Ablation may be the commenced, and the insulative suction cup may prevent lateral thermal spread of ablation energy.

Several ablation embodiments are possible: Fusion like or Epi-Sense electrode configuration with electrodes mounted along the sidewalls of the suction cup; Cryo probe tip mounted within the suction cup at the roof or along the sidewalls; Max Pen or Isolator Synergy style electrode configuration with or without internal cooling or contained irrigation; and Steerable catheter with distal cryo electrode or balloon and bipolar pacing/sensing leads In lieu of a suction applicator a magnetic epi/endo configuration, it may be possible whereby the magnets attract to immobilize the electrode with respect to clamped tissue. Since the epicardial magnet would need to be relatively large in size to sufficiently attract the endocardial ablation catheter/magnet it may be configured such that only a centralized portion was capable of conducting ablation energy in order to limit the ablation lesion size. In this configuration, either the epi or endo catheter could function as the roving catheter to perform electro-anatomical mapping and ID target ablation sites at which time the opposite magnetic/ablation pole would be coupled for bipolar epi/endo ablation Similar map, adhere or magnetize, and ablate systems could be adapted for atrial epicardial ablation by EPs. Such a system may be useful in addressing CFAEs epicardially by EPS with pericardial access/visualization. Additional experience with pericardial access and epicardial ablation by EPs may ultimately lead to EPs performing a significant portion of the lesion set epicardially (e.g. lateral lesions adjacent LPVs and RPVs and floor line) with existing/modified tools like a sub-X articulating/steerable Fusion. More advanced dissection tools may be necessary to dissect the pericardial reflections in order to access the transverse sinus to create the roof line of the LA.

Electrode/sensors could also be useful in other applications in conjunction with the aforementioned commercially available electro-anatomical mapping system. For example, locating such electrodes/sensor at the occlusion implant of a LAA occlusion system could help ensure its location at the base of the LAA prior to deploying potentially electrical isolation as visualized on a 3D electro-anatomical map.

Although the present methods and devices have been described in terms of the embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

What is claimed is:

1. A medical device for treating a surface area of tissue, the device comprising:
    a catheter body having a working end, wherein the catheter body comprises a multi-lumen configuration;
    a flexible body located at the working end of the catheter body, the flexible body having an expanse shape having a first expanse surface opposite to a second expanse surface, wherein the first expanse surface transmits energy to the surface area of tissue, where the flexible body is configured to assume a rolled configuration;
    at least one energy element on the first expanse surface, where the at least one energy element causes ablation of the surface area of tissue;
    a first chamber within the flexible body and adjacent to the first expanse surface, wherein the first chamber comprises a first chamber outer surface opposite to the first expanse surface;
    a second chamber within the flexible body and adjacent to the second expanse surface, wherein the second chamber is fluidly isolated from the first chamber, wherein the second chamber comprises a second chamber outer surface opposite to the second expanse surface;
    one or more suction lines exposed at a first edge of a perimeter of the first expanse surface;
    a plurality of sensing elements adjacent to the first expanse surface and configured to detect electrical activity in the surface area of tissue; and
    wherein delivery of a fluid through the catheter body and into the second chamber causes the flexible body to move from the rolled configuration to an unrolled configuration and also causes expansion of the second chamber to move the second expanse surface in a direction away from the first expanse surface such that adjacent tissues are further spaced from the surface area of tissue, wherein the second chamber outer surface contacts the first chamber outer surface when the flexible body is in the unrolled configuration, wherein the unrolled configuration comprises a planar configuration such that the first chamber outer surface is parallel to the second chamber outer surface and the first expanse surface is parallel to the second expanse surface, wherein the catheter body is configured to maintain fluid separation between the first chamber and the second chamber, wherein the one or more suction lines is configured to be attached to the tissue in the rolled configuration and the unrolled configuration, wherein the one or more suction lines holds the first edge of the flexible body in position during transition from the rolled configuration to the unrolled configuration via a second edge opposite the first edge; wherein the one or more suction lines are each individually coupled to a vacuum source.

2. The medical device of claim 1, further comprising a source of cooling fluid fluidly coupled to the first chamber, such that delivery of the cooling fluid to the first chamber causes ablation to the surface area of tissue through the first expanse surface.

3. The medical device of claim 1, wherein the at least one energy element comprises an RF electrode, a resistive electrode, a microwave antenna, and an electroporation electrode.

4. The medical device of claim 1, wherein the plurality of sensing elements are spaced in an array configuration adjacent to the first expanse surface.

5. The medical device of claim 1, where the one or more suction lines permits application of a vacuum therethrough.

6. The medical device of claim 1, wherein the flexible body comprises a first section having a first width and a second section having a second width, where the first width is less than the second width for positioning between pulmonary veins on an atrial surface.

7. The medical device of claim 1, wherein the second expanse surface comprises a thermally insulative surface.

8. The medical device of claim 1, further comprising at least one spline member within the flexible body.

9. The medical device of claim 1, wherein the catheter body extends between the first chamber and the second chamber.

10. The medical device of claim 1, wherein the catheter body extends along a side of the flexible body.

11. The medical device of claim 1, further comprising an ablation device comprising a sensing means, wherein the sensing means is configured to position the ablation device opposite to an area where a gap is detected in the surface area of the tissue.

* * * * *